United States Patent [19]

Childs

[11] 4,022,824

[45] May 10, 1977

[54] PERFLUOROCARBOXYLIC ACIDS FROM CARBOXYLIC ACIDS AND PERFLUOROCARBOXYLIC ACID FLUORIDES

[75] Inventor: William V. Childs, Bartlesville, Okla.

[73] Assignee: Phillips Petroleum Company, Bartlesville, Okla.

[22] Filed: June 2, 1975

[21] Appl. No.: 583,316

[52] U.S. Cl. .......................... 260/539 A; 260/408; 260/537 S; 260/539 R; 260/544 F
[51] Int. Cl.² .................. C07C 53/18; C07C 53/34
[58] Field of Search .......... 260/539 R, 539 A, 408, 260/537 S

[56] References Cited

UNITED STATES PATENTS

| 2,554,219 | 5/1951 | Simons et al. | 260/653 |
| 2,717,871 | 9/1955 | Scholberg et al. | 204/59 |
| 3,511,760 | 5/1970 | Fox et al. | 204/59 |
| 3,576,860 | 4/1971 | Zazaris | 260/541 |

OTHER PUBLICATIONS

Kirk Othmer, Encyclopedia of Chemical Technology, 2nd Ed., vol. 9, pp. 771–775.

*Primary Examiner*—Jane S. Myers

[57] ABSTRACT

Perfluorocarboxylic acids are produced by a metathesis reaction between an acid and a perfluoro acid fluoride (acyl fluoride). The perfluoroacyl fluoride can conveniently be produced by electrochemical fluorination of the acyl fluoride co-product of the metathesis step. As an alternate source of carboxylic acid, an acid anhydride can be cleaved with hydrogen fluoride. This also results in production of additional acyl fluoride which can be passed to an electrochemical fluorination cell to be converted to perfluoroacyl fluoride which can be recovered as product or additional free carboxylic acid can be introduced to utilize the extra perfluoroacyl fluoride to produce additional perfluoro acid.

10 Claims, 1 Drawing Figure

PERFLUOROCARBOXYLIC ACIDS FROM CARBOXYLIC ACIDS AND PERFLUOROCARBOXYLIC ACID FLUORIDES

BACKGROUND OF THE INVENTION

This invention relates to the production of perfluorocarboxylic acids.

Perfluorocarboxylic acids are items of commerce which have a broad scope of utility. For example, perfluorooctanoic acid can be used as a reagent to provide fluorine-containing groups on a polymer molecule thus imparting water-repellency and soil-resistance to fibers and fabrics prepared from such a modified polymer. Similarly, trifluoroacetic acid can be used as a catalyst and is a chemical intermediate in the production of pharmaceutical, agricultural, and industrial products.

The production of perfluorocarboxylic acids utilizing electrochemical techniques is known and recent developments in the field of electrochemical fluorination chemistry have made such techniques even more attractive. However, the primary cell products of such electrochemical fluorination techniques are invariably in the form of the acid fluorides, e.g., trifluoroacetyl fluoride. Thus, in order to obtain the desired perfluorocarboxylic acid, e.g., trifluoroacetic acid, this primary cell product must be hydrolyzed to obtain the free acid. Such hydrolysis can be wasteful of fluorine values in that the fluorine atom of the fluoroformyl group is either lost to the process or is not readily available for recycle because it becomes dissolved in water either as HF or as a fluoride salt.

It is also known in the field of electrochemical fluorination that carboxylic acid fluorides, e.g., acetyl fluoride, are more suitable as feedstocks for electrochemical fluorination than the corresponding free acids, e.g., acetic acid, because such an electrolysis can be carried out with greater smoothness and efficiency. However, the acid fluoride forms of the carboxylic acid are more inconvenient and costly feeds in that the free acid must be converted to the acyl fluoride in a separate and preliminary step.

SUMMARY OF THE INVENTION

It is an object of this invention to produce perfluorocarboxylic acids from free carboxylic acids;

it is the further object of this invention to avoid the loss of fluorine values encountered in the hydrolysis of acid fluorides;

it is the further object of this invention to utilize electrochemical fluorination to produce perfluoroacyl fluorides for reaction with free acids;

it is yet a further object of this invention to provide a water-free method converting a perfluorocarboxylic acid fluoride to the corresponding perfluorocarboxylic acid in a manner which essentially preserves the fluorine values of fluoroformyl group in the acyl fluoride for convenient reuse;

it is yet a further object of this invention to provide unitized combination process which conveniently utilizes more available and more economical free carboxylic acids as basic raw materials for the production of perfluorocarboxylic acids; and it is still yet a further object of this invention to produce perfluoro acids by a metathesis step wherein the free acid for this step, as well as acyl fluoride for electrochemical fluorination, is produced by hydrogen fluoride cleavage of carboxylic acid anhydride.

In accordance with this invention, a carboxylic acid is reacted with a perfluorocarboxylic acid fluoride to produce perfluorocarboxylic acid and carboxylic acid fluoride.

BRIEF DESCRIPTION OF THE DRAWING

The FIGURE, which forms a part hereof, shows in schematic form a simplified flow chart for the production of perfluorocarboxylic acid and optionally perfluoroacyl fluoride.

DESCRIPTION OF THE PREFERRED EMBODIMENTS

Figure 1:
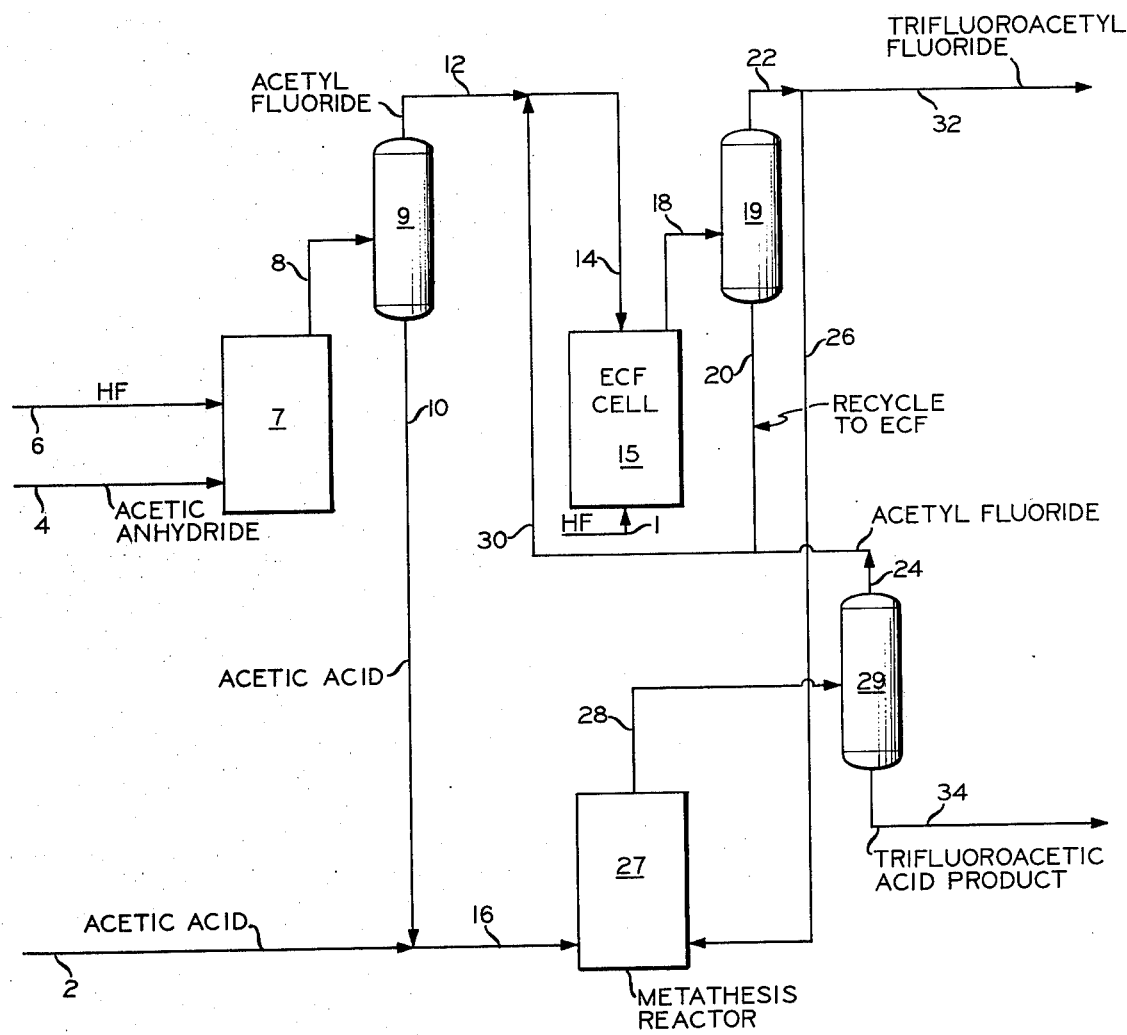

In accordance with Embodiment I of the present invention, perfluorocarboxylic acids are prepared by a procedure comprising:
1. contacting a carboxylic acid, under reaction conditions, with a perfluorocarboxylic acid fluoride to produce a carboxylic acid fluoride and a perfluorocarboxylic acid.

According to Embodiment II of the present invention, a carboxylic acid is converted to a perfluorocarboxylic acid by a procedure comprising:
1. contacting a carboxylic acid, under reaction conditions, with a perfluorocarboxylic acid fluoride to produce a carboxylic acid fluoride and a perfluorocarboxylic acid product;
2. subjecting the carboxylic acid fluoride from step (1) to electrochemical fluorination to produce a perfluorocarboxylic acid fluoride; and
3. passing the perfluorocarboxylic acid fluoride from step (2) to step (1).

According to Embodiment III of the present invention, a carboxylic acid anhydride is converted to a perfluorocarboxylic acid product and a perfluorocarboxylic acid fluoride co-product in a process combination which comprises:
1. contacting a carboxylic acid anhydride, under reaction conditions, with hydrogen fluoride to produce a carboxylic acid and a carboxylic acid fluoride;
2. contacting the carboxylic acid from step (1) with a perfluorocarboxylic acid fluoride, under reaction conditions, to produce a carboxylic acid fluoride and a perfluorocarboxylic acid product;
3. subjecting the carboxylic acid fluoride from (2) to electrochemical fluorination to produce a perfluorocarboxylic acid fluoride co-product; and
4. passing an amount of the perfluorocarboxylic acid fluoride from step (3) to step (2), said amount being sufficient to sustain the reaction of step (2).

According to Embodiment IV of the present invention, perfluorocarboxylic acid product together with varying amounts of perfluorocarboxylic acid fluoride co-product are prepared from both a carboxylic acid and a carboxylic acid anhydride in a process combination comprising:
1. contacting a carboxylic acid feedstock, under reaction conditions, with a perfluorocarboxylic acid fluoride to produce a carboxylic acid fluoride and a perfluorocarboxylic acid product;
2. contacting a carboxylic acid anhydride feedstock under reaction conditions, with hydrogen fluoride to produce a carboxylic acid and a carboxylic acid fluoride;
3. passing the carboxylic acid produced in step (2) to step (1) to augment the carboxylic acid feedstock used therein;

4. subjecting the carboxylic acid fluoride from step (1) and step (2) to electrochemical fluorination to produce a perfluorocarboxylic acid fluoride coproduct; and
5. passing an amount of the perfluorocarboxylic acid fluoride from step (4) to step (1), said amount being sufficient to sustain the reaction of step (1).

A number of advantages to the present invention in its various embodiments are now apparent. A primary electrochemical fluorination cell product, such as trifluoroacetyl fluoride for example, can now be conveniently and efficiently converted to the corresponding acid, such as trifluoroacetic acid, with no loss in fluorine values through hydrolysis. The fluorine atom of the fluoroformyl group is, in effect, transferred from a molecule of the fluorinated acid (acyl fluoride) to a molecule of the nonfluorinated acid and, thus, is in a form which is useful and in which the fluorine value is immediately recoverable.

Embodiment II of the present invention displays the advantage of providing a desirable and efficient carboxylic acid fluoride feed for the electrochemical fluorination step without the need for converting a free carboxylic acid to a carboxylic acid fluoride in a separate chemical step. In effect, the preparation of the desired feedstock and the formation of the desired product have now been combined into a single efficient step.

Embodiments III and IV of the present invention show still another advantage in that the process for the production of perfluorocarboxylic acids has been increased in its versatility. By employing the carboxylic acid anhydride as a primary feedstock or by employing a combination of a carboxylic acid and a carboxylic acid anhydride as primary feedstocks more than one product can be obtained and the relative amounts of these products can be easily controlled by controlling the relative amounts of these two feedstocks. Thus, in Embodiment IV, perfluorocarboxylic acid product and perfluorocarboxylic acid fluoride product can be produced over a wide ratio of proportions.

Although it is not intended to limit the scope of the present invention, the following simplified chemical equations can further describe and illustrate the chemical transformations involved in the present invention using specific exemplary feedstocks:

Embodiment I

Conversion of Perfluorocarboxylic Acid Fluoride to Perfluorocarboxylic Acid

Metathesis Step

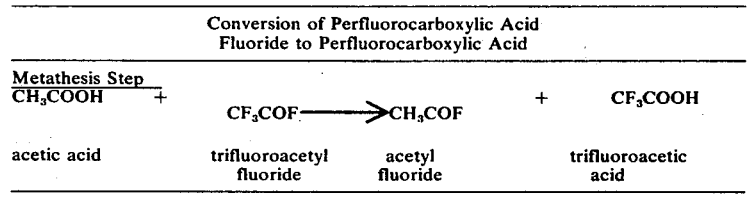

| $CH_3COOH$ | + | $CF_3COF$ | → | $CH_3COF$ | + | $CF_3COOH$ |
|---|---|---|---|---|---|---|
| acetic acid | | trifluoroacetyl fluoride | | acetyl fluoride | | trifluoroacetic acid |

The chemical equation above illustrates the efficient, convenient and novel conversion of a perfluorocarboxylic acid fluoride into the corresponding perfluorocarboxylic acid, thus completely avoiding the less desirable aqueous hydrolysis which is shown in the prior art for this transformation. Other higher carboxylic acids can undergo this transformation with similar advantage.

Embodiment II

Production of Perfluorocarboxylic Acid From Carboxylic Acid

Methathesis Step

| $CH_3(CH_2)_6COOH$ | + | $CF_3(CF_2)_6COF$ | → | $CH_3(CH_2)_6COF$ | + | $CF_3(CF_2)_6COOH$ |
|---|---|---|---|---|---|---|
| octanoic acid | | perfluorooctanoyl fluoride | | octanoyl fluoride | | perfluorooctanoic acid |

Electrochemical Fluorination Step

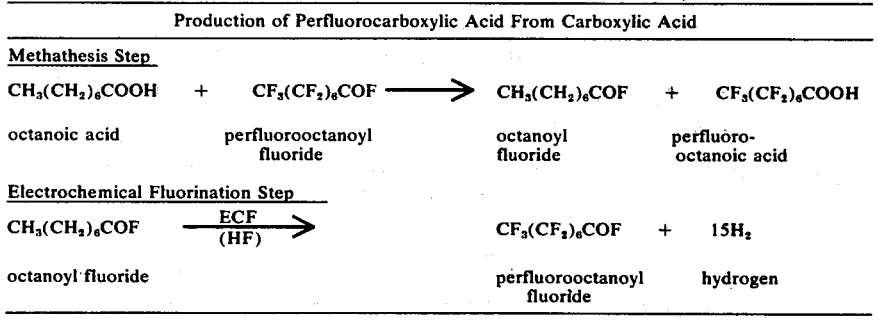

| $CH_3(CH_2)_6COF$ | $\xrightarrow[(HF)]{ECF}$ | $CF_3(CF_2)_6COF$ | + | $15H_2$ |
|---|---|---|---|---|
| octanoyl fluoride | | perfluorooctanoyl fluoride | | hydrogen |

The equations above illustrate a unique combination of steps which cooperate in a particularly advantageous way. In the metathesis step, the octanoic feed is converted to octanoyl fluoride which is a highly desirable form of this feedback for introduction to an electrochemical cell. That same metathesis step, advantageously, converts the corresponding perfluorooctanoyl fluoride to the desired perfluorooctanoic acid product. The electrochemical fluorination step which converts the octanoyl fluoride to its perfluoro derivative is shown to be a necessary and cooperating step in this process combination.

In theory, sufficient perfluorooctanoyl fluoride is generated in the electrochemical fluorination step to sustain the metathesis step. In actual operation, however, some mechanical and/or chemical losses of intermediates or products can be incurred. Therefore, to keep the process operating on a truly continuous basis it may be necessary to provide make-up amounts of the acyl fluoride, such as octanoyl fluoride, in minor amounts to the ECF step. This minor amount of make-up acyl fluoride can be obtained from any suitable source.

Embodiment III

Production of Perfluorocarboxylic Acid and Perfluorocarboxylic Acid Fluoride From Carboxylic Acid Anhydride Anhydride Cleavage Step

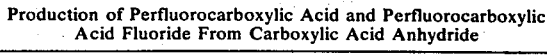

Embodiment III-continued

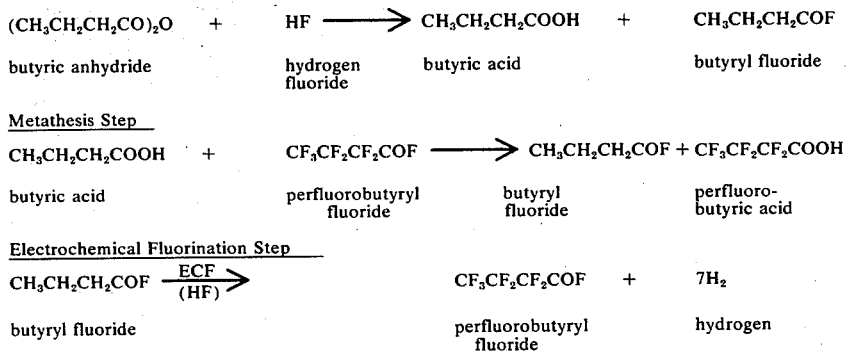

Production of Perfluorocarboxylic Acid and Perfluorocarboxylic Acid Fluoride From Carboxylic Acid Anhydride $(CH_3CH_2CH_2CO)_2O$ + $HF \longrightarrow CH_3CH_2CH_2COOH$ + $CH_3CH_2CH_2COF$ butyric anhydride    hydrogen fluoride    butyric acid    butyryl fluoride

Metathesis Step

$CH_3CH_2CH_2COOH$ + $CF_3CF_2CF_2COF \longrightarrow CH_3CH_2CH_2COF + CF_3CF_2CF_2COOH$ butyric acid    perfluorobutyryl fluoride    butyryl fluoride    perfluorobutyric acid

Electrochemical Fluorination Step

$CH_3CH_2CH_2COF \xrightarrow[(HF)]{ECF}$    $CF_3CF_2CF_2COF$ + $7H_2$ butyryl fluoride    perfluorobutyryl fluoride    hydrogen The equations above illustrate still another advantageous process combination in which three separate chemical transformations are combined in a way in which they cooperatively provide distinct advantages. The anhydride cleavage step, in which the butyric anhydride is efficiently converted, provides two different materials each of which is specifically useful in the process combination. The butyric acid product of this cleavage is, of course, immediately useful in the metathesis step while the butyryl fluoride cleavage product is, simultaneously, immediately useful in the electrochemical fluorination step.

Unlike Embodiment II, this embodiment enjoys the advantage of having no need for any externally provided make-up acyl fluoride feed to the ECF cell. Thus, though there may be mechanical and/or chemical losses within the process, there will be sufficient butyryl fluoride present to sustain the various steps in the process to provide a given amount of perfluorobutyric acid product. This is because butyryl fluoride is a coproduct of the process combination and will, therefore, always be available in amounts more than sufficient to provide the butyryl fluoride cell feed.

EMBODIMENT IV

Production of Perfluorocarboxylic Acid and Perfluorocarboxylic Acid Fluoride From Carboxylic Acid and Carboxylic Acid Anhydride The basic chemical equations involved in Embodiment IV are essentially identical to those described above in Embodiment III. The only, yet important, difference between Embodiment IV and Embodiment III is that Embodiment IV utilizes a carboxylic acid feedstock, such as acetic acid, together with a carboxylic anhydride feedstock, such as acetic anhydride, for example. The anhydride is cleaved with hydrogen fluoride to provide at least some of the acetic acid used in the metathesis step, and at least some of the acetyl fluoride used in the ECF step. By varying the amount of acetic acid with respect to acetic anhydride, the ratio of product and co-product can be closely controlled to correspond with the economic demand for each of these products. Thus, the products can be varied from about equimolar amounts of trifluoroacetyl fluoride and trifluoroacetic acid to essentially exclusively trifluoroacetic acid with little or none of the acetyl fluoride co-product. In the event that more trifluoroacetyl fluoride than trifluoroacetic acid is desired as product, the acetic anhydride can be utilized as the sole feed to the process and excess acetic acid can be removed as another co-product.

As mentioned earlier, some fluorine values can be lost in the process by the formation of minor amounts of some undesirable by-products such as, for example, fluoromethanes, fluoroethanes, and carbonyl fluoride. Any byproduct carbonyl fluoride, however, need not be rejected from the process but can be contacted with acetic acid in the metathesis step to produce carbon dioxide and acetyl fluoride. Alternatively, it can be contacted with acetic anhydride in the anhydride cleavage step to produce carbon dioxide and acetyl fluoride.

The feedstocks which are applicable for the various embodiments of the present invention are carboxylic acids such as mono- and dicarboxylic acids containing from 2 to about 10 carbon atoms per molecule, and their corresponding anhydrides. Some examples of these are saturated aliphatic hydrocarbon mono- and dicarboxylic acids and their corresponding anhydrides such as acetic acid, acetic anhydride, propionic acid, butyric acid, 3-methylbutyric acid, succinic acid, valeric acid, adipic acid, caproic acid, octanoic acid, decanoic acid, butyric anhydride, and the like, and mixtures thereof.

In Embodiment I wherein a carboxylic acid is reacted with a perfluorocarboxylic acid fluoride, the scope of the applicable fluorinated acid fluorides is the same as that of the nonfluorinated acids described above, that is, the acid fluorides contain from 2 to about 10 carbon atoms per molecule. In the other embodiments where the perfluoroacid fluoride for the metathesis step is generated by electrochemical fluorination of the acid fluoride product of the metathesis step, the acid and perfluoroacid fluoride will obviously have the same number of carbon atoms. Generally, in Embodiment I the reactants are chosen so as to have the same number of carbon atoms also.

A key step in all the embodiments of the present invention is the metathetical step in which a carboxylic acid is reacted with a perfluorocarboxylic acid fluoride. This has been found to be an efficient and convenient reaction. It is exothermic and can be substantially quantitative because, though an equilibrium reaction, high concentrations of the desired products are surprisingly favored. The molar proportions of carboxylic acid to perfluorinated carboxylic acid fluoride can vary depending upon convenience and the extent of conversion desired but will generally be in the range of from about 0.5:1 to 2:1. If quantitative or near quantitative conversion of the perfluorocarboxylic acid fluoride is desired, at least one mole, and preferably more, of carboxylic acid is present for each mole of the perfluorocarboxylic acid fluoride. Preferably, the molar ratio is in the range of 1:1 to about 1.3:1 moles of carboxylic acid to moles of perfluorocarboxylic acid fluoride.

The contact of these two materials can be carried out either batchwise or continuously under any suitable reaction conditions, including temperature, pressure and residence time, which will provide the desired degree of reaction. The temperature will generally be in the range of from about 0° to about 100° C, preferably from about 20° to about 25° C, and should be sufficiently high to maintain the reaction mixture in the liquid state. Acetic acid, for example, melts at 16.6° C. The reaction can be carried out at any convenient pressure and the pressure will generally be in the range of from 0 to about 1000 psig. The reaction time will generally be in the range from about 0.1 to about 100 minutes.

The step in which the carboxylic acid anhydride is cleaved with hydrogen fluoride can be carried out under any suitable conditions, including temperature, pressure and contact time, which are sufficient to provide the desired amounts of a corresponding carboxylic acid and the corresponding carboxylic acid fluoride. This reaction is exothermic, efficient, and can be substantially quantitative. The molar proportion of hydrogen fluoride to carboxylic acid anhydride can vary depending upon convenience and the desired degree of reaction. If essentially quantitative conversion of the anhydride is desired, one or more moles of hydrogen fluoride would be present for each mole of the anhydride. Generally, the molar ratio of hydrogen fluoride to anhydride will generally be in the range from about 0.5:1 to about .2:1, preferably 0.8:1 to about 1.5:1.

The temperature will generally be in the range of from about 0° to about 100° C, preferably from about 25° to about 75° C. Any convenient pressure can be used and the pressure will generally be in the range of from about 0 to about 1000 psig. The contact time will generally be in the range from about 0.1 to about 100 minutes.

The conversion of the carboxylic acid fluoride to the perfluorocarboxylic acid fluoride can be carried out using any suitable electrochemical fluorination procedure which is presently known in the art. Thus, electrochemical fluorination processes wherein the feedstock is dissolved in the liquid electrolyte, such as disclosed in U.S. Pat. No. 2,519,983, can be employed. Electrochemical processes wherein the feedstock is bubbled through a porous anode into the liquid electrolyte, such as disclosed in U.S. Pat. No. 3,298,940, can also be employed.

Particularly suitable are the electrochemical procedures disclosed in U.S. Pat. Nos. 3,511,760, 3,511,762, and 3,711,396, the contents of which are hereby incorporated into this disclosure by reference. The processes described in these patents feature a mode of reaction in which the fluorinatable feedstock, either in the presence or absence of a carrier gas, is passed into the pores of suitable porous anodes immersed in a suitable liquid electrolyte such that the feedstock and the resulting fluorinated products have no appreciable contact with the bulk of the liquid electrolyte outside the pores of the porous anode. Such a mode of operation has been found to offer significant advantages in efficiency and selectivity to desired products.

Briefly, said preferred electrochemical fluorination step comprises passing the vaporized carboxylic acid fluoride into the pores of a nonwetting porous anode, e.g., porous carbon, disposed in the current-conducting, essentially anhydrous hydrogen fluoride electrolyte such as KF·HF. The feedstock contacts the fluorinating species within the pores of the anode and is at least partially fluorinated therein. Ordinarily, the fluorination can be carried out at temperatures within the range of from about 50° to about 200° C at which the vapor pressure of the electrolyte is not excessive. More ordinarily, the preferred temperature range is from about 60° to 120° C. The fluorination can be carried out with any convenient pressure both above and below atmospheric and is generally carried out in the range of 0–500 psig.

The carboxylic acid fluoride is preferably introduced into the pores of an anode having a given porosity and permeability at a rate which is insufficient to bubble the feed into the bulk of the liquid electrolyte. That is, the feedstock is introduced into the porous anode at a point near its bottom and is permitted to exit the porous anode at a point near its top, preferably above the surface of the liquid electrolyte.

Current densities on the porous anode will generally be in the range of from about 25 to about 1000, preferably 50 to 300, milliamps per square centimeter of anode geometric surface area. The cell voltage will depend upon the geometry and materials in the cell but will generally be in the range of from 4 to 12 volts. The current and feed rates will ordinarily be such that from about 10 to about 100, preferably from about 50 to about 80, percent of the replaceable hydrogen in the total feedstock will be converted per pass through the cell. The FIGURE is a simplified flow diagram for the production of perfluorocarboxylic acid fluorides and perfluorocarboxylic acids. Although each of the chemical steps has been demonstrated using acetic acid and acetic anhydride as feedstocks, one skilled in the art will conclude that, because of similar chemical and physical properties, other homologous feedstocks can be used. However, for the sake of simplicity, the invention process in the FIGURE will be described in terms of converting acetic acid and acetic anhydride into trifluoroacetyl fluoride and trifluoroacetic acid.

In the FIGURE acetic anhydride and hydrogen fluoride are passed into anhydride cleavage zone 7 through lines 4 and 6, respectively. Cleavage zone 7 can comprise one or more reactors, in parallel or series, together with associated apparatus such as pumps, hold tanks, control devices, heat exchangers, and the like which are conventional and sufficient to facilitate the cleavage transformation. The reactor effluent from cleavage zone 7 passes through line 8 to separation zone 9.

Separation zone 9 can comprise one or more conventional separation means such as fractional distillation columns, absorption units, adsorption units, and the like together with associated pumps, heaters, heat exchangers, and the like which are sufficient to provide a separated stream consisting of essentially acetic acid in line 10. Separation zone 9 can also return (not shown) unreacted hydrogen fluoride, if any, and unreacted acetic anhydride, if any, to reaction zone 7 and can also reject (not shown) undesirable by-products, if any, from the process. It is to be noted that mixtures of hydrogen fluoride and acetic acid are extremely corrosive and the materials of construction in this area can advantageously include relatively inert materials such as Monel, Teflon, Kel-F, and the like.

Acetyl fluoride in line 12 is passed via line 14 into electrochemical fluorination (ECF) zone 15. Electrochemical fluorination zone 15 can comprise one or more electrolytic cells together with the associated pumps, regulators, electrodes, and the like which are conventional and sufficient to convert at least a portion of the acetyl fluoride to trifluoroacetyl fluoride. Hydrogen fluoride feedstock is fed to the electrolytic zone through line 1. Hydrogen (not shown) leaves this zone as a by-product. The effluent from the electrochemical fluorination zone 15 passes via line 18 into separation zone 19. This separation zone can be similar to separation zone 9 and is conventional and sufficient to provide a separated stream which consists essentially of partially fluorinated acetyl fluoride intermediates. These intermediates pass through line 20, through line 30, and finally through line 14 are recycled into the electrochemical fluorination zone 15. Undesirable light cell products or undesirable heavy cell products, if any, can be rejected (not shown) from separation zone 19.

A portion of the trifluoroacetyl fluoride in line 22 can be passed through line 32 as a product of the process pending any additional purification, if any. The remainder of the trifluoroacetyl fluoride passes from line 22 to line 26 into metathesis zone 27.

Metathesis zone 27 can comprise one or more chemical reactors and associated apparatus such as heat exchangers, control means, pumps, valves, and the like, which are sufficient to promote the reaction of trifluoroacetyl fluoride with acetic acid to produce acetyl fluoride and trifluoroacetic acid. Acetic acid is conducted into metathesis zone 27 by means of line 16 which comprises a mixture of virgin acetic acid feedstock in line 2 and cleavage acetic acid in line 10.

Effluent from metathesis zone 27 passes through line 28 into separation zone 29. Separation zone 29 can comprise one or more separation means and associated apparatus similar to separation zones 9 and 19 which are sufficient to provide a separated stream consisting essentially of acetyl fluoride in line 24 and a separated stream consisting essentially of trifluoroacetic acid in line 34. Acetyl fluoride in line 24 is blended with incompletely fluorinated intermediates from line 20, passed through line 30, blended with acetyl fluoride in line 12 and finally passed into electrochemical fluorination zone ECF through line 14. Undesirably heavy or light products, if any, can be rejected (not shown) from separation zone 29. Stream 34 consisting essentially of trifluoroacetic acid is removed from the process as product pending any additional purification, if any.

EXAMPLE I

In this example, trifluoroacetyl fluoride was reacted with glacial acetic acid in a one-step reaction to product trifluoroacetic acid and acetyl fluoride. The trifluoroacetyl fluoride feedstock, produced by electrochemical fluorination of acetyl fluoride, contained about 2 weight percent carbonyl fluoride by-product and about 0.6 weight percent hydrogen fluoride.

A gaseous stream of this feedstock was slowly bubbled into 28.82 g (0.48 mole) of glacial acetic acid contained in a 76 cc glass reaction tube immersed in a water bath. In addition to the acetic acid, the reaction tube also contained 3.05 g (0.030 mole) acetic anhydride to destroy the carbonyl fluoride and hydrogen fluoride contaminants in the feedstock.

A total of 49.7 g (0.43 mole) of the trifluoroacetyl fluoride feedstock was passed into the reaction tube over a period of about 1.5 hours. During this period the reaction pressure varied from about 0 to about 180 psig and the reaction temperature increased from about 19° C to about 43° C. The reaction mixture was then allowed to stand about 2 hours at room temperature.

Distillation of the reaction mixture yielded trifluoroacetic acid, acetyl fluoride, and acetic acid. A middle cut was taken and was confirmed by nuclear magnetic resonance (NMR) spectroscopy to be trifluoroacetic acid. This cut was analyzed by GLC and found to be greater than 99 weight percent pure, containing only minor amounts of acetic acid and acetyl fluoride. The material balance of the reaction was also consistent with the essentially quantitative reaction:

$$CF_3-\underset{\underset{O}{\|}}{C}-F \;+\; CH_3-\underset{\underset{O}{\|}}{C}-OH \;\longrightarrow\; CF_3-\underset{\underset{O}{\|}}{C}-OH \;+\; CH_3-\underset{\underset{O}{\|}}{C}-F.$$

Thus, the preceding example demonstrated the one-step reaction of Embodiment I of the present invention in that it showed the conversion of a perfluorocarboxylic acid fluoride to a perfluorocarboxylic acid.

CALCULATED ILLUSTRATIVE EXAMPLE II

To further illustrate the present invention, the following calculated example is provided to describe Embodiment IV of the present invention. Minor amounts of by-products and decomposition products have been neglected for simplicity.

In a continuous process substantially as described in the FIGURE, acetic acid, acetic anhydride, together with appropriate amounts of hydrogen fluoride, are converted to trifluoroacetyl fluoride and trifluoroacetic acid. In the anhydride cleavage zone 7, the temperature is maintained at about 50° C, the pressure at about 100 psig and the contact time at about 5 minutes. In the metathesis zone 27, the temperature is maintained at about 30° C, the pressure at about 25 psig, and the contact time at about 25 minutes.

In the electrochemical fluorination zone ECF, the KF·2HF electrolyte medium is maintained at about 105° C, the pressure is about 2 psig, the cathodes are iron, the anodes are porous carbon and the current density is about 200 ma/cm². The current and feed rates are such that 50 percent of the replaceable hydrogen is converted per pass through the cell.

Table I shows the chemical components in the principal streams in the process. The stream numbers correspond to those of the FIGURE.

Table I

| | | | | | | Stream Numbers (moles/hr) | | | | | | | | | | | |
|---|---|---|---|---|---|---|---|---|---|---|---|---|---|---|---|---|---|
| 1 | 2 | 4 | 6 | 8 | 10 | 12 | 14 | 16 | 18 | 20 | 22 | 24 | 26 | 28 | 30 | 32 | 34 |

Hydrogen

Table I-continued

| | Stream Numbers (moles/hr) | | | | | | | | | | | | | | | | | |
|---|---|---|---|---|---|---|---|---|---|---|---|---|---|---|---|---|---|---|
| | 1 | 2 | 4 | 6 | 8 | 10 | 12 | 14 | 16 | 18 | 20 | 22 | 24 | 26 | 28 | 30 | 32 | 34 |
| Fluoride | 600 | | | | 50 | | | | | | | | | | | | | |
| Acetic Anhydride | | | 50 | | | | | | | | | | | | | | | |
| Acetic Acid | | 100 | | | 50 | 50 | | | 150 | | | | | | | | | |
| Acetyl Fluoride | | | | | 50 | | 50 | 200 | | | | | 150 | | 150 | | | |
| Trifluoroacetyl Fluoride | | | | | | | | | | 200 | | 200 | | 150 | | 150 | 50 | |
| Partially Fluorinated Acetyl Fluorides | | | | | | | | 200 | | | 200 | 200 | | | | 200 | | |
| Trifluoroacetic Acid | | | | | | | | | | | | | | 150 | | | | 150 |

Thus, Table I illustrates Embodiment IV of the present invention wherein a combination of acetic acid and acetic anhydride feedstocks are shown to produce trifluoroacetic acid product with varying amounts of trifluoroacetyl fluoride co-product. It can be seen that the proportion of co-product can be increased by increasing the rate of acetic anhydride feedstock. Similarly, decreasing the anhydride feed rate decreases the rate of the co-product.

While this invention has been described in detail for the purpose of illustration, it is not to be construed as limited thereby but is intended to cover all changes and modifications within the spirit and scope thereof.

I claim:

1. A process comprising contacting under reaction conditions a mono- or dicarboxylic acid containing 2 to 10 carbon atoms, and a perfluorocarboxylic acid fluoride containing 2 to 10 carbon atoms to give a perfluorocarboxylic acid and an acyl fluoride.

2. A method in accordance with claim 1 wherein said contacting is carried out using a molar portion of carboxylic acid to perfluorocarboxylic acid fluoride in the range of 0.5:1 to 2:1 in a liquid state at a temperature within the range of 0°–100° C, a pressure within the range of 0–2000 psig, the contact time being in the range of 0.1–100 minutes.

3. A method in accordance with claim 1 wherein said perfluorocarboxylic acid fluoride has the same number of carbon atoms as said mono- or dicarboxylic acid, said mono- or dicarboxylic acid being a saturated aliphatic hydrocarbon mono- or dicarboxylic acid.

4. A method in accordance with claim 2 wherein said carboxylic acid is acetic acid, said perfluorocarboxylic acid fluoride is trifluoroacetyl fluoride, said perfluorocarboxylic acid is trifluoroacetic acid and said acyl fluoride is acetyl fluoride.

5. A method according to claim 1 wherein said acyl fluoride is passed to an electrochemical fluorination zone.

6. A method according to claim 5 wherein said perfluorocarboxylic acid fluoride is provided by recycle of the product from said electrochemical fluorination step.

7. A method according to claim 1 wherein said carboxylic acid is provided by anhydride cleavage of a corresponding acid anhydride with HF.

8. A method according to claim 7 wherein said acyl fluoride is passed through an electrochemical fluorination step to produce said perfluorocarboxylic acid fluoride for recycle to said contacting step.

9. A method according to claim 8 wherein additional free acid is introduced into said contacting step and wherein acyl fluoride from said cleavage step is passed to said electrochemical fluorination step to provide additional amounts of said perfluorocarboxylic acid fluoride.

10. A method according to claim 1 wherein an acid anhydride is cleaved with HF and wherein all of the acyl fluoride required in the process is produced by said cleavage step and by said contacting step.

* * * * *